United States Patent
Olivera et al.

(10) Patent No.: US 9,241,830 B2
(45) Date of Patent: Jan. 26, 2016

(54) PRESSURE MONITOR FOR PNEUMATIC VITRECTOMY MACHINE

(75) Inventors: Argelio Olivera, Mission Viejo, CA (US); Mark Hopkins, Mission Viejo, CA (US); Denis Turner, Vista, CA (US)

(73) Assignee: Novartis AG, Basel (CH)

( * ) Notice: Subject to any disclaimer, the term of this patent is extended or adjusted under 35 U.S.C. 154(b) by 2242 days.

(21) Appl. No.: 11/611,443

(22) Filed: Dec. 15, 2006

(65) Prior Publication Data
US 2008/0146988 A1  Jun. 19, 2008

(51) Int. Cl.
  G05D 11/00 (2006.01)
  A61F 9/007 (2006.01)
  F15B 19/00 (2006.01)
  A61B 17/00 (2006.01)

(52) U.S. Cl.
  CPC ........... *A61F 9/00736* (2013.01); *F15B 19/005* (2013.01); *A61B 2017/00544* (2013.01); *F15B 2211/30565* (2013.01); *F15B 2211/3138* (2013.01); *F15B 2211/31576* (2013.01); *F15B 2211/327* (2013.01); *F15B 2211/6313* (2013.01); *F15B 2211/87* (2013.01); *F15B 2211/8755* (2013.01); *Y10T 137/2544* (2015.04)

(58) Field of Classification Search
  CPC ................. A61B 2017/00544; Y10T 137/2544
  USPC ............ 137/102, 106, 487.5, 625.65, 596.12, 137/596.17
  See application file for complete search history.

(56) References Cited

U.S. PATENT DOCUMENTS

| | | | |
|---|---|---|---|
| 812,162 A | 2/1906 | Bemis | |
| 2,016,746 A | 10/1935 | Ireland | |
| 2,707,389 A | 5/1955 | Fortier | |
| 3,084,674 A | 4/1963 | Watson | |
| 3,646,727 A | 3/1972 | Wachsmuth | |
| 3,703,139 A | 11/1972 | Furlong | |
| 3,726,307 A * | 4/1973 | Carman et al. | 137/487.5 |
| 3,867,934 A | 2/1975 | Ollivier | |
| 4,075,928 A * | 2/1978 | Bitonti | 91/29 |

(Continued)

FOREIGN PATENT DOCUMENTS

| | | |
|---|---|---|
| DE | 39 25 405 A1 | 2/1991 |
| DE | 42 32 586 A1 | 3/1994 |

(Continued)

OTHER PUBLICATIONS

Office Action, U.S. Appl. No. 11/554,387, filed Sep. 17, 2009, 23 pages.

(Continued)

*Primary Examiner* — Kevin Murphy
(74) *Attorney, Agent, or Firm* — Darien Reddick (57) ABSTRACT

A system for a pneumatically-powered vitrectomy machine includes an output port, a venting valve, a venting manifold, a pressure transducer, and a controller. The output port provides pressurized gas to a vitrectomy probe. The venting valve is located close to the output port. The venting manifold fluidly connects the venting valve to a venting port. The venting port vents pressurized gas from the venting manifold. The pressure transducer is located near the output port. The pressure transducer is configured to read a pressure of a gas near the output port. The controller is adapted to receive information about the pressure and activate the venting valve. When the information received from the pressure transducer indicates a fault condition, the controller directs the venting valve to open.

10 Claims, 4 Drawing Sheets

(56) References Cited

U.S. PATENT DOCUMENTS

| | | | |
|---|---|---|---|
| 4,077,567 | A | 3/1978 | Ginn et al. |
| 4,086,804 | A | 5/1978 | Ruby |
| 4,253,480 | A | 3/1981 | Kessel et al. |
| 4,323,064 | A | 4/1982 | Hoenig et al. |
| 4,331,130 | A | 5/1982 | Lewicky |
| 4,344,144 | A | 8/1982 | Damico et al. |
| 4,449,550 | A | 5/1984 | Ranalli |
| 4,476,532 | A | 10/1984 | Akiyama et al. |
| 4,590,935 | A | 5/1986 | Ranalli |
| 4,622,503 | A | 11/1986 | Sunblom et al. |
| 4,650,460 | A | 3/1987 | Roizenblatt |
| 4,650,462 | A | 3/1987 | Desatnick et al. |
| 4,679,583 | A | 7/1987 | Lucas et al. |
| 4,706,687 | A | 11/1987 | Rogers et al. |
| 4,757,814 | A | 7/1988 | Wang et al. |
| 4,770,654 | A | 9/1988 | Rogers et al. |
| 4,790,816 | A | 12/1988 | Sunblom et al. |
| 4,810,242 | A | 3/1989 | Sundblom et al. |
| 4,840,111 | A | 6/1989 | Garnjost |
| 4,887,636 | A * | 12/1989 | Rothen ............... 137/487.5 |
| 4,933,843 | A | 6/1990 | Scheller et al. |
| 5,094,260 | A | 3/1992 | Stuart et al. |
| 5,138,838 | A * | 8/1992 | Crosser ............... 60/433 |
| 5,176,628 | A | 1/1993 | Charles et al. |
| 5,239,861 | A | 8/1993 | Fujita et al. |
| 5,279,322 | A * | 1/1994 | Nakamura et al. ........ 137/102 |
| 5,314,295 | A | 5/1994 | Lukkari et al. |
| 5,318,072 | A * | 6/1994 | Goedecke ............... 137/884 |
| 5,323,953 | A | 6/1994 | Adderley et al. |
| 5,417,246 | A | 5/1995 | Perkins et al. |
| 5,549,139 | A | 8/1996 | Perkins et al. |
| 5,571,248 | A | 11/1996 | Seetharaman et al. |
| 5,580,347 | A | 12/1996 | Reimels |
| 5,587,536 | A | 12/1996 | Rasmussen |
| 5,674,194 | A | 10/1997 | Jung et al. |
| 5,829,335 | A | 11/1998 | Ewald et al. |
| 5,846,257 | A | 12/1998 | Hood |
| 5,857,485 | A | 1/1999 | Perkins et al. |
| 5,979,494 | A | 11/1999 | Perkins et al. |
| 6,065,494 | A * | 5/2000 | Thomsen et al. ........ 137/552 |
| 6,155,233 | A | 12/2000 | Wade et al. |
| 6,155,289 | A | 12/2000 | Carlsen et al. |
| 6,391,102 | B1 | 5/2002 | Bodden et al. |
| 6,450,966 | B1 | 9/2002 | Hanna |
| 6,474,289 | B1 | 11/2002 | Lilly et al. |
| 6,514,268 | B2 | 2/2003 | Finlay et al. |
| 6,575,990 | B1 | 6/2003 | Wang et al. |
| 6,655,404 | B2 * | 12/2003 | Hilaire ............... 137/86 |
| 6,773,445 | B2 | 8/2004 | Finlay et al. |
| 6,779,541 | B2 | 8/2004 | Inayama et al. |
| 7,089,733 | B1 * | 8/2006 | Jackson et al. ........ 60/422 |
| 7,244,240 | B2 | 7/2007 | Nazarifar et al. |
| 7,335,217 | B2 | 2/2008 | Wang et al. |
| 7,470,277 | B2 | 12/2008 | Finlay et al. |
| 7,814,936 | B2 | 10/2010 | Catron |
| 2002/0069916 | A1 * | 6/2002 | Ferguson et al. ........ 137/487.5 |
| 2002/0117214 | A1 | 8/2002 | Tucker et al. |
| 2002/0173814 | A1 | 11/2002 | Jung et al. |
| 2002/0174905 | A1 * | 11/2002 | Latino et al. ............ 137/884 |
| 2003/0042182 | A1 | 3/2003 | Moscaritolo |
| 2003/0078609 | A1 | 4/2003 | Finlay et al. |
| 2005/0060974 | A1 | 3/2005 | Palmerton et al. |
| 2006/0086251 | A1 | 4/2006 | Sprinkle |
| 2006/0271082 | A1 | 11/2006 | Kirchhevel et al. |
| 2007/0270735 | A1 | 11/2007 | Williams et al. |
| 2007/0270746 | A1 | 11/2007 | King |
| 2007/0282262 | A1 | 12/2007 | Williams et al. |
| 2008/0082077 | A1 | 4/2008 | Williams |
| 2008/0142093 | A1 | 6/2008 | Turner et al. |
| 2008/0146988 | A1 | 6/2008 | Olivera et al. |
| 2008/0149197 | A1 | 6/2008 | Turner et al. |
| 2008/0168985 | A1 | 7/2008 | Turner et al. |
| 2008/0147429 | A1 | 12/2008 | Turner et al. |
| 2009/0124962 | A1 | 5/2009 | Hopkins et al. |
| 2009/0183630 | A1 | 7/2009 | Vroman et al. |
| 2009/0203480 | A1 | 8/2009 | Petzold et al. |
| 2009/0259242 | A1 | 10/2009 | Gerg et al. |
| 2009/0270793 | A1 | 10/2009 | Domash et al. |

FOREIGN PATENT DOCUMENTS

| | | |
|---|---|---|
| DE | 198 21 420 C1 | 10/1999 |
| DE | 10247869 A1 | 5/2004 |
| DE | 10341477 | 3/2005 |
| DE | 20 2005 009670 U1 | 9/2005 |
| DE | 10247869 B4 | 2/2007 |
| EP | 0469641 B1 | 6/1989 |
| EP | 0626628 A1 | 11/1994 |
| EP | 0626628 B1 | 12/1997 |
| EP | 0 884 667 A1 | 6/1998 |
| EP | 0673475 B1 | 6/1998 |
| EP | 874163 A2 | 10/1998 |
| EP | 1 172 586 A1 | 1/2002 |
| EP | 1660244 B1 | 12/2006 |
| EP | 1734260 A2 | 12/2006 |
| EP | 2032878 | 12/2009 |
| GB | 792397 | 3/1958 |
| GB | 1 213 723 | 11/1970 |
| GB | 2 016 746 A | 9/1979 |
| GB | 2 389 423 A | 12/2003 |
| JP | 61-18133 | 3/1982 |
| JP | 62-203437 | 12/1987 |
| JP | 5-87779 | 1/1989 |
| JP | 2-223846 | 9/1990 |
| JP | 07259801 A | 10/1995 |
| JP | 09225698 A | 9/1997 |
| JP | 10-339301 | 12/1998 |
| WO | WO 95/31141 A1 | 11/1995 |
| WO | WO 00/78371 A1 | 12/2000 |
| WO | WO 01/64120 A1 | 9/2001 |
| WO | WO 2008/000599 A1 | 1/2008 |
| WO | WO 2008/054944 A1 | 5/2008 |
| WO | WO 2008/105950 A2 | 9/2008 |
| WO | WO 2008/105950 A3 | 9/2008 |
| WO | WO 2008/140537 A1 | 11/2008 |
| WO | WO 2008/147429 A2 | 12/2008 |
| WO | WO 2008/147429 A3 | 12/2008 |

OTHER PUBLICATIONS

International Searching Authority, PCT International Preliminary Report on Patentability, PCT/US2007/079915, May 15, 2009, 6 pages.

International Searching Authority, PCT International Preliminary Report on Patentability, PCT/US2007/080265, Sep. 1, 2009, 8 pages.

International Searching Authority, PCT International Preliminary Report on Patentability, PCT/US2007/080540, Jun. 23, 2009, 5 pages.

Office Action, U.S. Appl. No. 11/610,275, filed Sep. 14, 2009, 18 pages.

International Searching Authority, PCT International Preliminary Report on Patentability, PCT/US2007/080239, Jun. 16, 2009, 8 pages.

Office Action, U.S. Appl. No. 11/610,275, filed Nov. 25, 2008, 10 pages.

Office Action, U.S. Appl. No. 11/610,275, filed Apr. 13, 2009, 16 pages.

Kabei, Shimemura, et al., A portable pneumatic driving unit for a left ventricular assist device, Int. J. Artif. Organs, 1988, 186-90, 11(3).

Nachlas, Marvin, et al., A simple portable pneumatic pump for external cardiac massage, The American Journal of Cardiology, 1962, 107-109, 10(1).

J.L. Waldeck; "The Development of a Portable Pressure Source for the Static and Dynamic Calibration of Pressure Transducers"; Journal of Wind Engineering and Industrial Aerodynamics, 1987, 26(2), 213-230.

Ellis, George, et al., Microcomputer-Controlled Precision Pressure Generator, IEEE Transactions on Instrumentation and Measurement, 1977, 214-217, 26(3).

Whalen, R.L., et al., An electromagnetic pneumatic blood pump driver, American Society of Artificial Internal Organs, 1988, 721-725, 34(3).

(56) References Cited

OTHER PUBLICATIONS

Turkentine, R.B., et al., Pressure-operated shutter for thin-film monitor, Journal of Physics E: Scientific Instruments, 1979, 12(1).
Rogers, Richard C., An inexpensive picoliter-volume pressure ejection system, Brain Research Bulletin, 1985, 669-671, 15(6).
Johnson, Kenneth S., et al., A submersible flow analysis System, Analytical Chimica Acta, 1986, 245-257, 179.
Tabassum, Alim Abid, Solar refrigeration: evaluation of technical options and design of a solar-generator-adsorber for a novel adsorption refrigerator, Cranfield Univ., 1989.
Buchanan, P.R., et al., Recovery of ventilation distributions by gas wash-out of a mechanical pump, Clinical Physics and Physiological Measurement, 1986, 7(3).
International Search Report for PCT/US2007/080239, Publication No. WO2008/140537, 3 pages.
International Search Report for PCT/US2007/079915, Publication No. WO2008/054944, 2 pages.
International Search Report for PCT/US2007/080265, Publication No. WO2008/105950, 3 pages.
International Search Report for PCT/US2007/080540, Publication No. WO2008/147429, 4 pages.
Document labeled "D1A" titled "oerHi Switzerland" received in an opposition filed Dec. 2, 2011 in the corresponding EP Patent No. EP2099399; Granted Mar. 2, 2011, 4 pages.
Document labeled "D1B" titled "Pneumatik Einheit" received in an opposition filed Dec. 2, 2011 in the corresponding EP Patent No. EP2099399; Granted Mar. 2, 2011, 1 page.
Document labeled "D1C" entitled "OS3 Basic: Pneumatik" received in an opposition filed Dec. 2, 2011 in the corresponding EP Patent No. EP2099399; Granted Mar. 2, 2011, 1 page.
Document labeled "D1D" entitled "SPS Highspeed Vitrektomie Stripper" received in an opposition filed Dec. 2, 2011 in the corresponding EP Patent No. EP2099399; Granted Mar. 2, 2011, 1 page.
Document labeled "D1E" and "D2E" entitled "Oertli Instrumente AG/Alcon Inc.-Eidesstattliche Erklarung" received in an opposition filed Dec. 2, 2011 in the corresponding EP Patent No. EP2099399; Granted Mar. 2, 2011, 8 pages.
English translation of document labeled "D1E" and "D2E" entitled "Oertli Instrumente AG/Alcon Inc.-Affidavit" received in an opposition filed Dec. 2, 2011 in the corresponding EP Patent No. EP2099399; Granted Mar. 2, 2011, 3 pages.
Document labeled "D1F" entitled "Strukturstuckliste" received in an opposition filed Dec. 2, 2011 in the corresponding EP Patent No. EP2099399; Granted Mar. 2, 2011, 2 pages.
Document labeled "D2A" entitled "Kopie" received in an opposition filed Dec. 2, 2011 in the corresponding EP Patent No. EP2099399; Granted Mar. 2, 2011, 5 pages.
Document labeled "D2B" entitled "Oertli Instrumente AG, PN210062d" received in an opposition filed Dec. 2, 2011 in the corresponding EP Patent No. EP2099399; Granted Mar. 2, 2011, 1 page.
Document labeled "D2C" entitled "OS Basic: Pneumatik; Fast VIT-PN" received in an opposition filed Dec. 2, 2011 in the corresponding EP Patent No. EP2099399; Granted Mar. 2, 2011, 1 page.
Document labeled "D2D" entitled "SPS Highspeed Vitrektomie Stripper" received in an opposition filed Dec. 2, 2011 in the corresponding EP Patent No. EP2099399; Granted Mar. 2, 2011, 1 page.
Document labeled "D2F" entitled "Service Manual, OS3 Basic" received in an opposition filed Dec. 2, 2011 in the corresponding EP Patent No. EP2099399; Granted Mar. 2, 2011, 25 pages.
Document labeled "D2G" entitled "Stuckliste-Pneumatik Einheit" received in an opposition filed Dec. 2, 2011 in the corresponding EP Patent No. EP2099399; Granted Mar. 2, 2011, 2 pages.
Document labeled "D2H" entitled "Stuckliste-Pneumatikeinheit SMC Ventile" received in an opposition filed Dec. 2, 2011 in the corresponding EP Patent No. EP2099399; Granted Mar. 2, 2011, 1 page.
Document labeled "D2I" entitled "Application Note" received in an opposition filed Dec. 2, 2011 in the corresponding EP Patent No. EP2099399; Granted Mar. 2, 2011, 4 pages.
Document labeled "D3" entitled "U.S. Pat. No. 5,417,246" received in an opposition filed in the corresponding EP Patent No. EP2099399; Granted Mar. 2, 2011, 30 pages.
Document labeled "Electronic Receipt" entitled "Empfangsbescheinigung" received in an opposition filed in the corresponding EP Patent No. EP2099399; Granted Mar. 2, 2011, 2 pages.
Document labeled "EP Notice of Opposition—German" entitled "Einspruch gegen ein europaisches Patent" received in an opposition filed Dec. 2, 2011 in the corresponding EP Patent No. EP2099399; Granted Mar. 2, 2011, 5 pages.
English translation of document labeled "Notice of Opposition—German" entitled "Opposition to EP 2099399 of Alcon Inc." received in an opposition filed Dec. 2, 2011 in the corresponding EP Patent No. EP2099399; Granted Mar. 2, 2011, 15 pages.
Document labeled "Notice of Opposition—German" entitled "Isler & Pedrazzini AG" received in an opposition filed Dec. 2, 2011 in the corresponding EP Patent No. EP2099399; Granted Mar. 2, 2011, 18 pages.
Response to Invitation for Opposition, dated Jan. 24, 2012, for the corresponding EP Patent No. EP2099399; Granted Mar. 2, 2011; 9 pages.
Decision Revoking European Patent, dated Aug. 25, 2014, for the corresponding EP Patent No. EP2099399; Granted Mar. 2, 2011, 1 page.
Notice of Opposition from Isler & Pedrazzini AG dated Sep. 8, 2014, for the corresponding EP Patent No. EP2099399; Granted Mar. 2, 2011, 135 pages.
Partial English translation of Notice of Opposition from Isler & Pedrazzini AG dated Sep. 8, 2014, for the corresponding EP Patent No. EP2099399; Granted Mar. 2, 2011, 4 pages.

\* cited by examiner

PRESSURE MONITOR FOR PNEUMATIC VITRECTOMY MACHINE

FIELD OF INVENTION

The present invention relates to a pneumatic module for a surgical machine and more particularly to a monitor and gas release valve located near the output end of a vitrectomy machine.

BACKGROUND OF THE INVENTION

Several conditions of the eye threaten sight. Epiretinal membrane (ERM), also known as macular pucker and cellophane retinopathy, is a condition characterized by growth of a membrane across the macula, or central retina of the eye. This condition may be thought of as the growth of scar tissue across the macula, thus interfering with central vision. The ERM typically contracts, causing distortion of the central retina, thus producing distortion of vision. Most patients will note that either straight objects appear wavy and crooked and/or central vision is reduced, depending on the severity of the condition.

Epiretinal membranes may be associated with other conditions of the eye, however, the large majority are idiopathic, which means that the cause is unknown. Some of the disorders which are occasionally associated with ERM's include previous retinal detachments and surgery thereof, inflammatory conditions (uveitis), retinal tears, and branch retinal vein occlusion (BRVO) and central retinal vein occlusion (CRVO).

Another condition is a macular hole. A macular hole is almost always a spontaneous development that occurs predominantly in aging women. The development of a macular hole progresses through several stages, and with each progressive stage the vision may worsen. It has been postulated that shrinkage of the vitreous humor may produce traction on the fovea (central macula), thereby producing the hole itself. However, the cause of macular holes remains under investigation.

The retina, which lines the inside of the posterior wall of the eye, may occasionally become detached for various reasons. Most commonly, retinal detachment occurs as a result of a tear or hole in the retina, which develops as a result of a posterior vitreous separation (PVS). The retinal tear or hole allows fluid to enter the subretinal space, thus detaching the retina.

The retina receives oxygen and nutrients from the underlying choroid (vascular layer) of the eye. When a retinal detachment occurs, the detached retina begins to dysfunction, and ultimately, necrosis (death) ensues as a result if the retina is not reattached to the underlying choroid. As such, a retinal detachment is an urgent condition. The detached retina should be recognized and treated promptly.

Vitreo-retinal procedures may be appropriate to treat these and other serious conditions of the back of the eye. Vitreo-retinal procedures include a variety of surgical procedures performed to restore, preserve, and enhance vision. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It makes up approximately ⅔ of the eye's volume, giving it form and shape before birth. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

The retinal surgeon performs a vitrectomy with a microscope and special lenses designed to provide a clear image of the back of the eye. Several tiny incisions just a few millimeters in length are made on the sclera. The retinal surgeon inserts microsurgical instruments through the incisions such as a fiber optic light source to illuminate inside the eye, an infusion line to maintain the eye's shape during surgery, and instruments to cut and remove the vitreous.

In a vitrectomy, the surgeon creates three tiny incisions in the eye for three separate instruments. These incisions are placed in the pars plana of the eye, which is located just behind the iris but in front of the retina. The instruments which pass through these incisions include a light pipe, an infusion port, and the vitrectomy cutting device. The light pipe is the equivalent of a microscopic high-intensity flashlight for use within the eye. The infusion port is required to replace fluid in the eye and maintain proper pressure within the eye. The vitrector, or cutting device, works like a tiny guillotine, with an oscillating microscopic cutter to remove the vitreous gel in a controlled fashion. This prevents significant traction on the retina during the removal of the vitreous humor.

The surgical machine used to perform a vitrectomy and other surgeries on the posterior of the eye is very complex. Typically, such an ophthalmic surgical machine includes a main console to which numerous different tools are attached. The main console provides power to and controls the operation of the attached tools.

The attached tools typically include probes, scissors, forceps, illuminators, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

In order to provide pneumatic power to the various tools, the main surgical console has a pneumatic or air distribution module. This pneumatic module conditions and supplies compressed air or gas to power the tools. Typically, the pneumatic module is connected to a cylinder that contains compressed gas. Most commonly, surgeons use cylinders of nitrogen at 3600 psi. The condition and output of these cylinders affect the operation of the surgical machine.

The proper gas pressure must be provided by the pneumatic module to the tools in order to insure their proper operation. Providing too high a gas pressure can lead to operational problems. Too high a pressure can damage equipment or lead to a malfunction during surgery. In either case, the instrument itself may be damaged.

It would be desirable to incorporate a gas pressure system in an ophthalmic surgical machine to protect the equipment.

SUMMARY OF THE INVENTION

In one embodiment consistent with the principles of the present invention, the present invention is a system for a pneumatically-powered vitrectomy machine. The system includes a first output port, a venting valve, a first venting manifold, a first pressure transducer, and a controller. The first output port provides pressurized gas to a vitrectomy probe. The venting valve is located close to the first output port. The first venting manifold fluidly connects the venting valve to a first venting port. The first venting port vents pressurized gas from the first venting manifold. The first pressure transducer is located near the first output port. The first pressure transducer is configured to read a first pressure of a gas near the first output port. The controller is adapted to receive information about the first pressure and activate the venting valve. When the information received from the first pressure transducer indicates a fault condition, the controller directs the venting valve to open.

In another embodiment consistent with the principles of the present invention, the present invention is a system for a pneumatically-powered vitrectomy machine. The machine includes first and second output ports, first and second venting manifolds, first and second pressure transducers, an output valve, a venting valve, and a controller. The first and second output ports provide pressurized gas to a vitrectomy probe. The output valve directs pressurized gas to the first output port and the second output port. The venting valve is located close to the first output port and the second output port. The first venting manifold connects the venting valve to a first venting port. The first venting port vents pressurized gas from the first venting manifold. The second venting manifold connects the venting valve to a second venting port. The second venting port vents pressurized gas from the second venting manifold. The first pressure transducer is located near the first output port and is configured to read a first pressure of a gas near the first output port. The second pressure transducer is located near the second output port and is configured to read a second pressure of a gas near the second output port. The controller is adapted to receive information about the first pressure and the second pressure and activate the venting valve. When the information received from the first or second pressure transducer indicates a fault condition, the controller directs the venting valve to open.

In another embodiment consistent with the principles of the present invention, the present invention is a method of operating a pneumatically-powered vitrectomy machine. A first pressure of a gas near a first output port to which a vitrectomy probe is attached is monitored. A second pressure of a gas near a second output port to which the vitrectomy probe is attached is monitored. A fault condition based on the first or second pressure is detected. A venting valve is opened after the fault condition has been detected.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
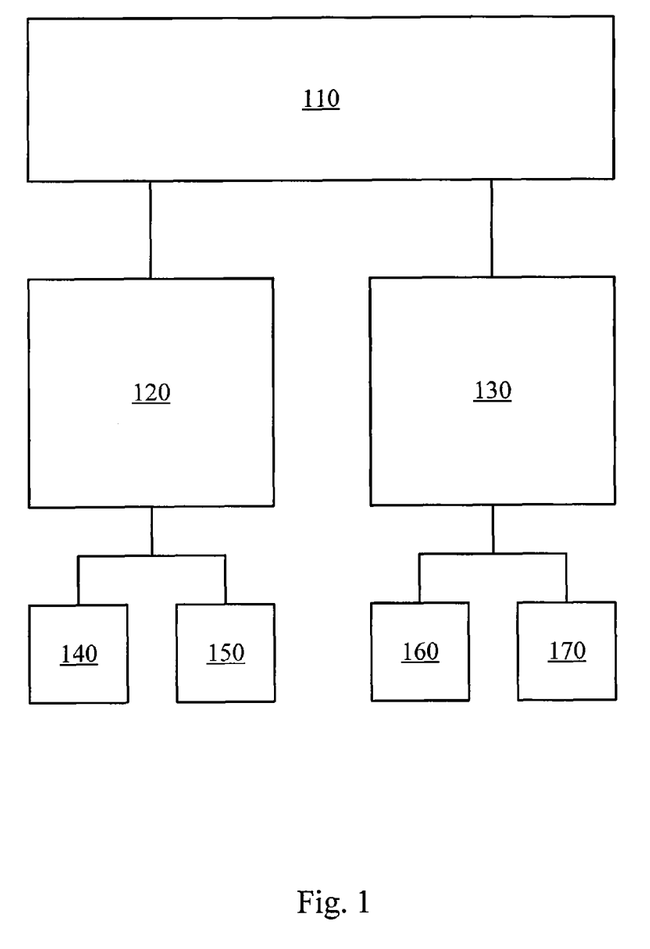
FIG. 1 is a block diagram of a pneumatically-powered ophthalmic surgery machine according to an embodiment of the present invention.

FIG. 1 is a block diagram of a pneumatically powered ophthalmic surgical machine according to an embodiment of the present invention. In FIG. 1, the machine includes gas pressure monitor system 110, proportional controller 120, proportional controller 130, and tools 140, 150, 160, and 170. The tools 140, 150, 160, and 170 can be, for example, scissors, vitrectomy probes, forceps, and injection or extraction modules. Other tools may also be employed with the machine of FIG. 1.

As shown in FIG. 1, gas pressure monitor system 110 is fluidly coupled via a manifold to proportional controller 120 and proportional controller 130. A single manifold may connect gas pressure monitor system 110 to proportional controller 120 and proportional controller 130, or two separate manifolds may connect gas pressure monitor system 110 to proportional controller 120 and proportional controller 130, respectively. Proportional controller 120 is fluidly coupled to tools 140 and 150 by, for example, a manifold and tubing. Likewise proportional controller 130 is fluidly coupled to tools 160 and 170 by, for example, a manifold and tubing.

In operation, the pneumatically powered ophthalmic surgery machine of FIG. 1 operates to assist a surgeon in performing various ophthalmic surgical procedures, such as a vitrectomy. A compressed gas, such as nitrogen, provides the power for tools 140, 150, 160, and 170. The compressed gas passes through gas pressure monitor system 110, through one or more manifolds to proportional controllers 120 and 130, and through additional manifolds and/or tubing to tools 140, 150, 160, and 170.

Gas pressure monitor system 110 functions to monitor the pressure of compressed gas from a gas source as it enters the machine. Proportional controllers 120 and 130 serve to distribute the compressed gas received from gas pressure monitor system 110. Proportional controllers 120 and 130 control the pneumatic power delivered to tools 140, 150, 160, and 170. Various valves, manifolds, and tubing are used to direct compressed gas from gas pressure monitor system 110, through proportional controllers 120 and 130, and to tools 140, 150, 160, and 170. This compressed gas actuates cylinders, for example, in tools 140, 150, 160, and 170.

Figure 2:
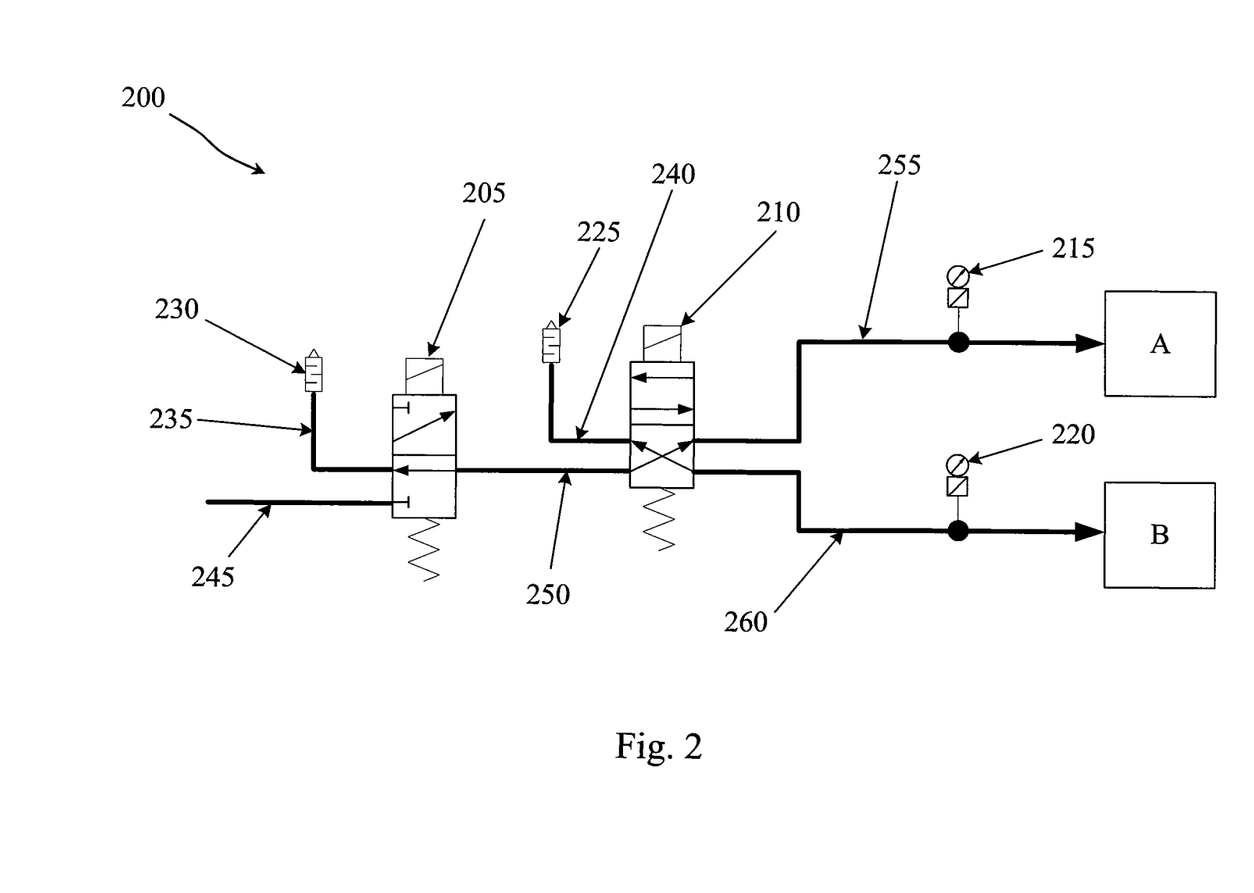
FIG. 2 is a schematic of a pressure monitor system for a pneumatically powered vitrectomy machine according to an embodiment of the present invention.

FIG. 2 is a schematic of a pressure monitor system for a pneumatically powered vitrectomy machine according to an embodiment of the present invention. In FIG. 2, the pressure monitor system includes venting valve 205, output valve 210, pressure transducers 215 and 220, mufflers 225 and 230, venting manifolds 235 and 240, manifolds 245, 250, 255, and 260, and output ports A and B.

Venting manifold 235 fluidly connects venting valve 205 to muffler 230. Manifold 245 is also fluidly connected to venting valve 205. Venting valve 205 is fluidly connected to output valve 210 by manifold 250. Venting manifold 240 fluidly connects output valve 210 to muffler 225. Manifold 255 fluidly connects output valve 210 to output port A. Manifold 260 fluidly connects output valve 210 to output port B. Pressure transducer 215 is fluidly connected to manifold 255. Likewise, pressure transducer 220 is fluidly connected to manifold 260.

In the embodiment of FIG. 2, venting valve 205 is a standard two-way valve. As is commonly known, the valve has a solenoid that operates to move the valve to one of the two positions depicted in FIG. 2. As shown, the valve is in a venting position. Pressurized gas can pass from manifold 250, through venting valve 205, through venting manifold 235, and out of muffler 230. In the other position, venting valve 205 allows pressurized gas to pass from manifold 245, through venting valve 205, and into manifold 250 where it can provide power to the vitrectomy probe (not shown). Venting valve 205 is controlled by a controller (not shown).

Output valve 210 is a standard four-way valve. As is commonly known, the valve has a solenoid that operates to move the valve to one of the two positions depicted in FIG. 2. As shown in FIG. 2, the valve is in a position to provide pressurized gas to output port A, and to vent pressurized gas from output port B. In this position, pressurized gas can pass from manifold 250, through output valve 210, through manifold 255, and to output port A where the pressurized gas provides pneumatic power to a vitrectomy probe (not shown). Pressurized gas in manifold 260 can pass through output valve 210, venting manifold 240, and muffler 225 where it is exhausted to the atmosphere. In the other position, output valve 210 allows pressurized gas to pass from manifold 250, through output valve 210, through manifold 260, and to output port B where the pressurized gas provides pneumatic power to a vitrectomy probe (not shown). Pressurized gas in manifold 255 can pass through output valve 210, venting manifold 240, and muffler 225 where it is exhausted to the atmosphere. Output valve 210 is controlled by a controller (not shown).

The vitrectomy probe (not shown) that is attached to output ports A and B acts as a cutting device. The cutter is moved by a cylinder that in turn is moved by pressurized gas. The cylinder oscillates as pressurized gas is alternately directed to output ports A and B. Such a vitrectomy device is designed to provide about 5,000 cuts per minute.

Pressure transducers 215 and 220 operate to read an atmospheric pressure of the gas contained in manifolds 255 and 260, respectfully. In other words, pressure transducer 215 reads the pressure of the compressed gas that is adjacent to it in manifold 255. Likewise, pressure transducer 220 reads the pressure of the compressed gas that is adjacent to it in manifold 260. In the embodiment of FIG. 2, pressure transducers 215 and 220 are common pressure transducers. Pressure transducers 215 and 220 are capable of reading pressure of a compressed gas and sending an electrical signal containing information about the pressure of the compressed gas to a controller (not shown).

Manifolds 235, 240, 245, 250, 255, and 260 are all configured to carry compressed gas. In the embodiment of FIG. 2, these manifolds are machined out of a metal, such as aluminum. These manifolds are air tight, contain various fittings and couplings, and are designed to withstand relatively high gas pressures. These manifolds maybe manufactured as individual pieces or they maybe manufactured as a single piece. For example, manifolds 235, 240, 245, 250, 255, and 260 may be machined from a single piece of aluminum.

Mufflers 225 and 230 are common mufflers designed to suppress the noise made by escaping gas. These mufflers are typically cylindrical in shape.

In operation, pressurized gas is directed alternately to output ports A and B to operate the vitrectomy probe. Venting valve 205 is operated in a position that allows pressurized gas to pass from manifold 245, through venting valve 205, and into manifold 250. Output valve 210 is alternated between its two positions very rapidly to provide pressurized gas to output ports A and B. In one position, pressurized gas can pass from manifold 250, through output valve 210, through manifold 255, and to output port A where the pressurized gas provides pneumatic power to a vitrectomy probe (not shown). Pressurized gas in manifold 260 can pass through output valve 210, venting manifold 240, and muffler 225 where it is exhausted to the atmosphere. In the other position, output valve 210 allows pressurized gas to pass from manifold 250, through output valve 210, through manifold 260, and to output port B where the pressurized gas provides pneumatic power to a vitrectomy probe (not shown). Pressurized gas in manifold 255 can pass through output valve 210, venting manifold 240, and muffler 225 where it is exhausted to the atmosphere. Output valve 210 is controlled by a controller (not shown).

In this manner, pressurized gas is provided to output port A while pressurized gas in manifold 260 is allowed to vent through a venting port to which muffler 225 is attached. Likewise, pressurized gas is provided to output port B while pressurized gas in manifold 255 is allowed to vent through a venting port to which muffler 225 is attached. Due to the quick response of the output valve selected, pressurized gas can be alternated very quickly between manifolds 255 and 260. This allows the vitrectomy probe (not shown) to operate at very high cut rates of about 5,000 cuts per minute.

Pressure transducers 215 and 220 monitor the system for a fault condition. When a fault condition is detected in the vitrectomy probe, the pressurized gas is vented to prevent damage to the equipment. In this case, venting valve 205 is in the position shown in FIG. 2. In this case, pressurized gas can pass from manifold 250, through venting valve 205, through venting manifold 235, and out of a venting port to which muffler 230 is attached. In the valve positions shown in FIG. 2, pressurized gas in manifold 260 can pass through output valve 210, venting manifold 240, and out of a venting port to which muffler 225 is attached. Pressurized gas in manifold 255 can pass through output valve 210, manifold 250, venting valve 205, venting manifold 235, and out of a venting port to which muffler 230 is attached. If the output valve is in the other position, pressurized gas in manifold 255 can pass through output valve 210, venting manifold 240, and out of a venting port to which muffler 225 is attached. Pressurized gas in manifold 260 can pass through output valve 210, manifold 250, venting valve 205, venting manifold 235, and out of a venting port to which muffler 230 is attached.

As noted, pressure transducers 215 and 220 monitor the gas pressure in manifolds 255 and 260, respectively. Pressure transducers 215 and 220 detect fault conditions that may be present during the operation of the vitrectomy probe. In one fault condition, the gas pressure in one or both manifolds 215 and 220 may exceed a threshold thereby posing a threat to the equipment. In such a case, the vitrectomy probe may be damaged.

The placement of venting valve 205 close to the output ports A and B allows gas to be quickly vented, effectively turning off the vitrectomy probe to prevent damage to the probe. In general, the faster the pressurized gas can be exhausted from the system in the event of a fault condition, the more likely it is that damage can be prevented.

Figure 3:
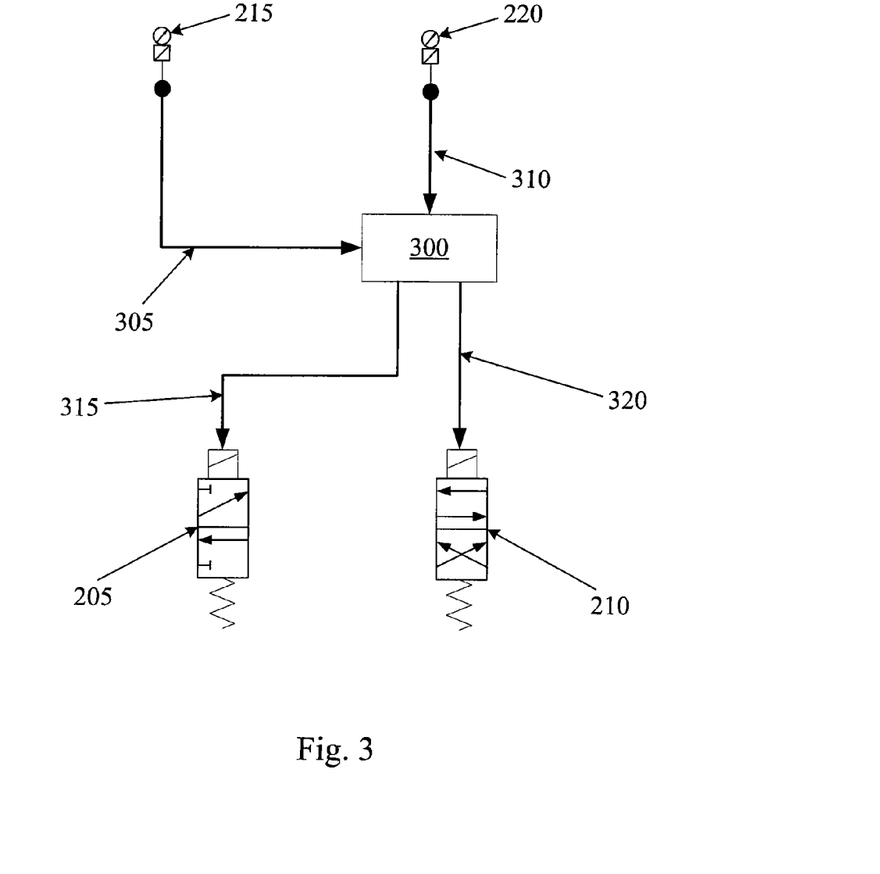
FIG. 3 is a schematic of a portion of a pressure monitor system for a pneumatically powered vitrectomy machine according to an embodiment of the present invention.

FIG. 3 is a schematic of a portion of a pressure monitor system for a pneumatically powered vitrectomy machine according to an embodiment of the present invention. In FIG. 3, controller 300 and interfaces 305, 310, 315, and 320 are depicted along with venting valve 205, output valve 210, and pressure transducers 215 and 220.

In the embodiment of FIG. 3, controller 300 receives pressure information from pressure transducers 215 and 220 via interfaces 305 and 310, respectively. In this manner, pressure transducer 215 is electrically coupled to controller 300 via interface 305, and pressure transducer 220 is electrically coupled to controller 300 via interface 310. Controller sends control signals to venting valve 205 and output valve 210 via interfaces 315 and 320, respectively.

Controller 300 is typically an intergraded circuit capable of performing logic functions. In this manner, controller 300 is in the form of a standard integrated circuit package with power, input, and output pins. In various embodiments, controller 300 is a valve controller or a targeted device controller. In such a case, controller 300 performs specific control functions targeted to a specific device, such as a valve. In other embodiments, controller 300 is a microprocessor. In such a case, controller 300 is programmable so that it can function to control valves as well as other components of the machine. In other cases, controller 300 is not a programmable microprocessor, but instead is a special purpose controller configured to control different valves that perform different functions.

Controller 300 is configured to receive signals from pressure transducer 215 via interface 305 and from pressure transducer 220 via interface 310. These signals, for example, correspond to readings of gas pressure in manifolds 255 and 260, respectively. Controller 300 is also configured to send output signals via interfaces 315 and 320 to venting valve 205 and output valve 210, respectively. These output signals allow controller 300 to control the operation of venting valve 205 and output valve 210.

Interfaces 305 and 310 are designed to carry signals from pressure transducers 215 and 220 to controller 300. In this case, interfaces 305 and 310 are common electrical conductors such as wires. Likewise, interfaces 315 and 320 carry signals from controller 300 to venting valve 205 and output valve 210. Interfaces 305, 310, 315, and 320 may be one or more wires or buses designed to carry electrical or data signals.

Figure 4:
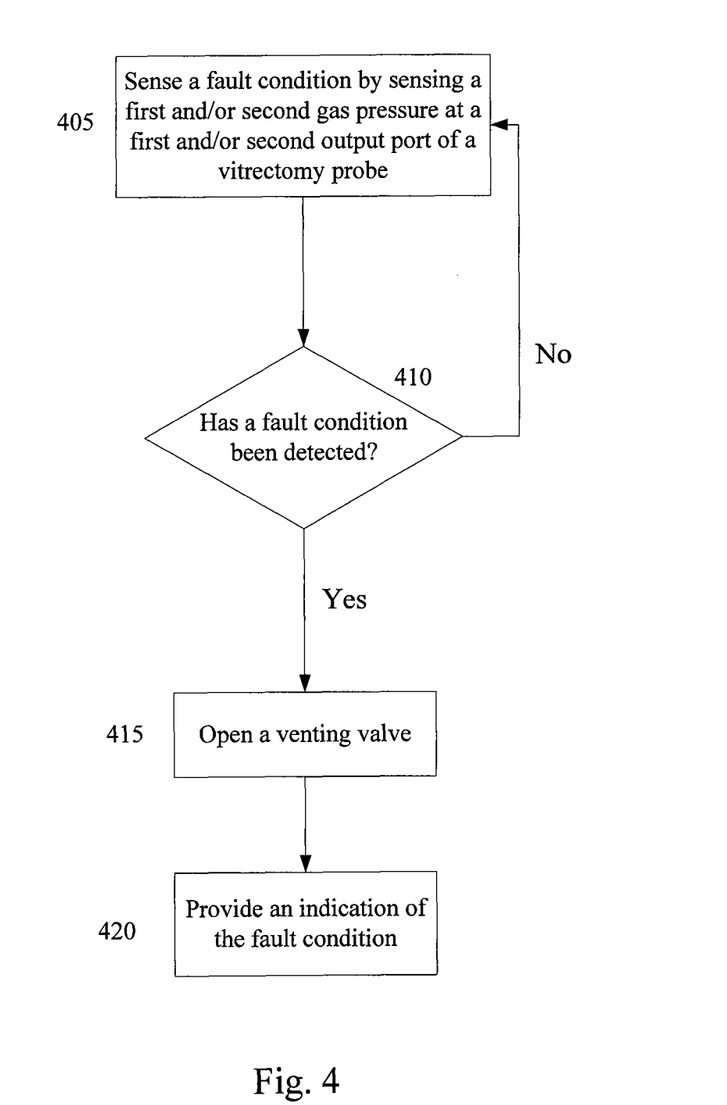
FIG. 4 is a flow chart of one method of operation according to an embodiment of the present invention.

FIG. 4 is a flow chart of one method of operation according to an embodiment of the present invention. In FIG. 4, one method of operating the pressure monitor system of FIGS. 2 and 3 is described. In 405, a fault condition is sensed by sensing a first and/or second gas pressure at a first and/or second output port of a vitrectomy probe. In 410, a determination is made as to whether a fault condition has been detected. If a fault condition has been detected, then in 415, a venting valve is opened, and in 420, and indication of the fault condition is provided. If a fault condition has not been detected in 410, then the method returns to 405.

The indication of a fault condition, which in some instances is a high gas pressure, can be provided visually or audibly. If visually, a light emitting diode may be illuminated, an indication may appear on a display, or a similar visual event may occur. If audibly, a warning sound may be emitted. Any other type of indication or combination of visual and audible indications may be provided in accordance with the various embodiments of the present invention.

From the above, it may be appreciated that the present invention provides an improved system and methods for monitoring the gas pressure in a pneumatic module of a vitrectomy machine. The present invention provides features designed to protect the equipment from harm due to high gas pressure. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for a pneumatically-powered vitrectomy machine comprising:
   a source of pressurized gas;
   a first output port for providing pressurized gas to a vitrectomy probe;
   a second output port for providing pressurized gas to the vitrectomy probe;
   an output valve operable to selectively direct pressurized gas to the first output port and the second output port, the output valve in selective communication with the source of pressurized gas;
   a first manifold coupling the first output to the output valve;
   a second manifold coupling the second output port to the output valve;
   a first venting manifold connecting the output valve to a first venting port, the output valve movable between a first position in which pressurized gas is supplied to the first output port and pressurized gas from the second manifold is vented via the first venting port and a second position in which pressurized gas is supplied to the second output port and pressurized gas from the first manifold is vented via the first venting port;
   a venting valve disposed between the source of pressurized gas and the output valve;
   a second venting manifold connecting the venting valve to a second venting port, the venting valve moveable between a first position in which pressurized gas from the output valve is vented via the second venting port and pressurized gas from the source of pressurized gas is prevented from being communicated to the output valve and a second position in which pressurized gas from the source of pressurized gas is communicated to the output valve;
   a first pressure transducer disposed in the first manifold, the first pressure transducer configured to read a first pressure of a gas in the first manifold; and
   a controller adapted to receive information received from the first pressure and activate the venting valve;
   wherein when the information received from the first pressure transducer indicates a fault condition, the controller directs the venting valve into the first position;
   wherein in the controller is adapted to rapidly oscillate the output valve between the first position and the second position, the alternatingly supplied pressurized gas operable to oscillate a cutter of the vitrectomy probe.

2. The system of claim 1 further comprising:
   a second pressure transducer disposed in the second manifold, the second pressure transducer configured to read a second pressure of a gas in the second manifold.

3. The system of claim 2 wherein when the information received from the second pressure transducer indicates a fault condition, the controller directs the venting valve into the first position.

4. The system of claim 1 further comprising a muffler attached to the first venting port.

5. The system of claim 1 wherein the fault condition is indicated by a high gas pressure.

6. The system of claim 1 wherein the output valve is located between the venting valve and the first output port.

7. The system of claim 6 wherein the output valve is a four-way valve and the venting valve is a two-way valve.

8. The system of claim 1, wherein the output valve is a solenoid-operated valve.

9. The system of claim 1, wherein the venting valve is a solenoid-operated valve.

10. The system of claim 1, wherein the first manifold, the second manifold, the first venting manifold, and the second venting manifold are formed into a piece of metal.

* * * * *